United States Patent
Tu et al.

[11] Patent Number: 6,090,134
[45] Date of Patent: Jul. 18, 2000

[54] SURFACE FLUORINATED STENT AND METHODS THEREOF

[75] Inventors: Lily Chen Tu; Hosheng Tu, both of Tustin, Calif.

[73] Assignee: Polymerex Medical Corp., San Diego, Calif.

[21] Appl. No.: 09/250,316

[22] Filed: Feb. 16, 1999

[51] Int. Cl.[7] .................................................. A61F 2/06
[52] U.S. Cl. ........................................................... 623/1
[58] Field of Search .................................. 606/191, 194, 606/108, 198, 158; 623/1.11, 1.19, 1.21, 1.42, 1.49, 11, 12

[56] References Cited

U.S. PATENT DOCUMENTS

| | | | |
|---|---|---|---|
| 3,953,566 | 4/1976 | Gore | 264/288 |
| 4,632,842 | 12/1986 | Karwoski et al. | 427/2 |
| 4,718,907 | 1/1988 | Karwoski et al. | 623/12 |
| 4,733,665 | 3/1988 | Palmaz | 128/343 |
| 5,100,429 | 3/1992 | Sinofsky et al. | 623/1 |
| 5,246,451 | 9/1993 | Trescony et al. | 623/1 |
| 5,665,114 | 9/1997 | Weadock et al. | 623/1 |
| 5,810,870 | 9/1998 | Myers et al. | 606/198 |
| 5,824,046 | 10/1998 | Smith et al. | 623/1 |

*Primary Examiner*—Michael Buiz
*Assistant Examiner*—Vy Q. Bui

[57] ABSTRACT

An intraluminal medical device for treating tissues in a patient, the device comprising an elongate radially expandable tubular stent having an interior luminal surface and an opposite exterior surface extending along a longitudinal stent axis; the interior luminal surface, the exterior surface, and/or an entire surface of the expandable tubular stent having fluorine-containing coating to render the surface biocompatible and/or hemocompatible.

14 Claims, 4 Drawing Sheets

SURFACE FLUORINATED STENT AND METHODS THEREOF

FIELD OF THE INVENTION

The present invention generally relates to improved intraluminal medical device and methods for treating tissues. More particularly, the present invention relates to such a surface fluorinated stent for supporting and reinforcing an enlarged vessel having a beneficial advantage of reduction in restenosis.

BACKGROUND OF THE INVENTION

A stent is a generally longitudinal tubular device formed of biocompatible material, preferably a metallic or a plastic material, which is useful in the treatment of stenosis, strictures or aneurysms in body vessels such as blood vessels. It is well known to employ a stent for the treatment of diseases of various body vessels. The device is implanted either as a "permanent stent" within the vessel to reinforce collapsing, partially occluded, weakened or abnormally dilated sections of the vessel or as a "temporary stent" for providing therapeutic energy treatment to the diseased vessels. Stents are typically employed after angioplasty of a blood vessel to prevent restenosis of the diseased vessel. Stents may be useful in other body vessels such as the urological tract and bile duct. The temporary stent is defined in this invention as a stent that is expandable inside a vessel and retractable thereafter from the vessel of a patient.

Stents generally include an open flexible configuration. The stent configuration allows the stent to be configured in a radially compressed state for intraluminal catheter insertion to an appropriate site. Once properly positioned adjacent the damaged vessel, the stent is radially expanded so as to support and reinforce the vessel. Radial expansion of the stent may be accomplished by an inflatable balloon attached to the catheter or the stent may be of the self-expanding type that will radially expand once deployed. One stent example is U.S. Pat. No. 4,733,665 to Palmaz, which is incorporated by reference herein, An expanded PTFE (ePTFE) vascular graft is well known to have a substantially non-thrombogenic fluorinated surface. An ePTFE patch is also used for repairing the ruptured blood vessel wall. An ePTFE graft and its process of making are well known to one who is skilled in the art. One ePTFE example is U.S. Pat. No. 3,953,566, which teaching is incorporated herein by reference.

U.S. Pat. No. 5,810,870 to Myers et al. discloses a stent covered by an ePTFE to take the advantage of the substantially non-thrombogenic properties of a fluorinated surface, wherein the ePTFE cover exhibits suitable expansion capabilities so as to enable the cover to expand upon expansion of the underlying stent. The ePTFE covered stent exposes the fluorinated ePTFE surface, not the stent surface, to the underlying tissue or the flowing blood stream. Occasionally, the ePTFE cover might shift itself from its associated stent because the ePTFE cover is loosely covering the stent. This misalignment phenomenon of an ePTFE cover on a stent becomes a clinical problem when the stent is non-retractably deployed because the ePTFE cover does not firmly adhere to the stent structure. Said ePTFE covered stent blocks the openness of the stent and does not allow blood to continuously provide nutrient to the tissue behind the implanted stent. Tissue necrosis might occur due to inadequate perfusion, especially for a long ePTFE-covered stent.

U.S. Pat. No. 5,824,046 to Smith et al. also teaches the advantage of the substantially non-thrombogenic surface property by covering the stent with an unsintered PTFE. The fluorinated surface of the covered stent by covering with an unsintered PTFE is biocompatible; however, the unsintered PTFE layer or sheet only loosely covers the stent structure and might shift from its intended position onto a stent. The covered stent by an unsintered PTFE still does not allow blood to continuously supply nutrient to the underlying tissue behind the stent. This might cause cells necrosis and result in vessel re-stenosis.

Therefore, there is an urgent clinical need to provide a surface fluorinated stent or a stent having its surface coated by fluorine-containing material while still preserve the openness of the stent configuration, such as a coil stent, a mesh stent, a scaffold stent, a sleeve stent, a porous stent, or a permeable stent. Preferably, the stent material surface is coated or adhered by fluorine, fluoride, or fluorine-containing material while the stent open surface structure is open for blood perfusion to the tissue of vessel walls.

U.S. Pat No. 4,632,842 to Karwoski et al., U.S. Pat. No. 4,718,907 to Karwoski et al., and U.S. Pat. No. 5,246,451 to Trescony et al. disclose one fluorine-containing coating technique for coating fluorine, fluoride, or fluorine-containing compound onto the surface of a substrate to have a very low surface energy and to be essentially non-thrombogenic. However, none of the above-referred patents teaches coating fluorine, fluoride, or fluorine-containing compounds onto a stent that has a very small stent material surface to open surface ratio. Other preferred techniques of depositing fluorine-containing material onto a stent include dipping, dip coating, pasting (or paste coating), and/or sintering processes.

Furthermore, RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

A stent deployed within a vessel, such as a coronary stent, has excellent metal-to-tissue contact surface. It becomes an ideal medium for applying thermal energy to the tissue needed for treatment or modulation. RF energy can be applied to a surface fluorinated stent to render the stent less prone to re-stenosis. Therefore, there is a need for an improved intraluminal medical device having a fluorinated surface and the capability to contact the inner walls of a tubular vessel using the radiofrequency energy to effectively treat and support/reinforce an enlarged artery or other tissues.

SUMMARY OF THE INVENTION

In general, it is an object of the present invention to provide an intraluminal medical device comprising a surface fluorinated stent or surface fluorinated grafted stent for intraluminal medical applications. It is another object to provide a process of making same and method for using same for a surface fluorinated stent or grafted stent. It is a further object of the present invention to provide an ablation system by using an external RF generator for providing RF energy through the surface fluorinated stent to an underlying tissue for therapeutic treatment.

In one preferred embodiment, an intraluminal medical device comprises an elongate radially expandable tubular stent having an interior luminal surface and an opposite exterior surface extending along a longitudinal stent axis. The stent in this invention may include a permanent implantable stent, an implantable grafted stent, or a temporary stent, wherein the temporary stent is defined in this invention as a stent that is expandable inside a vessel and retractable thereafter from the vessel of a patient. The stent configuration may be selected from a group consisting of a coil stent, a memory coil stent, a Nitinol stent, a mesh stent, a scaffold stent, a sleeve stent, a permeable stent, a stent having a temperature sensor, a porous stent, and the like. The stent may be deployed by an inflatable balloon on a catheter, by a self-deployable mechanism after released from a catheter, or by other appropriate means. The elongate radially expandable tubular stent may be a grafted stent, wherein the grafted stent is a composite device having a stent inside or outside of a graft. The graft may be a vascular graft, such as an ePTFE graft, a biological graft, or a woven graft.

In one embodiment, the exterior surface of the expandable tubular stent of the intraluminal medical device of the present invention has fluorine-containing coating. The exterior surface of a stent having fluorine-containing compound is to render the tissue-contacting surface biocompatible. It is well known to one who is skilled in the art that a fluorinated surface has low surface energy and is highly biocompatible and hemo-compatible compatible. The "fluorine-containing surface" is synonymous in this invention to "fluorinated surface", which substrate surface is covered or impregnated with fluorine, fluoride, other fluorine-containing compounds, and the like.

In an alternate embodiment, the interior luminal surface or an entire surface of the elongate radially expandable tubular stent of the intraluminal medical device of the present invention has fluorine-containing compounds. The interior luminal surface having fluorine-containing coating is to render the fluid contacting surface biocompatible or blood compatible. The fluorine-containing coating and its process may be selected from a group consisting of glow discharge coating, adhesive coating, impregnating coating, compound coating, dip coating, paste coating, and sintering. The dip coating and paste coating on a metallic substrate followed by sintering has been extensively used to coat the frying pans and the like, and is well known to one who is skilled in the art. One class of the fluorine-containing material used in said coating process has a tradename of Teflon® (a tradename of Du Pont Company).

U.S. Pat No. 4,632,842 to Karwoski et al., U.S. Pat. No. 4,718,907 to Karwoski et al., and U.S. Pat. No. 5,246,451 to Trescony et al. disclose a glow discharge coating technique for coating fluorine-containing compounds onto the surface of a substrate to have a very low surface energy and to be essentially non-thrombogenic. Said patents are incorporated herein by reference. The process for making a surface fluorinated stent includes deposition onto the stent of a fluorine-containing coating by inducing glow discharge progressively along the stent inside a reaction vessel. A polymerizable fluorine-containing gas, such as tetrafluoroethylene and the like, is flown through the stent in the reaction vessel. A radiofrequency field is applied to the gas within the vessel so that a fluorine-containing compound is deposited onto the surface of the stent. In the case of coating one side of the stent, only the surface to be coated is exposed to the glow discharged fluorine-containing gas.

Alternately, a process for making a surface of an intraluminal medical device biocompatible comprises surface treatment means for coating or depositing fluorine or a fluorine-containing material on the surface of the intraluminal medical device. The intraluminal medical device may be an elongate radially expandable tubular stent, an elongate radially expandable tubular grafted stent and the like. The surface treatment means for coating/depositing fluorine or a fluorine-containing material on the surface of the intraluminal medical device may be selected from a group consisting of glow discharge coating, adhesive coating, impregnating coating, compound coating, dip coating, paste coating, and sintering. The treated surface is selected from a group consisting of an interior luminal surface, an exterior surface or an entire surface of the intraluminal medical device. The stent may be made of a porous material to enhancing fluorine deposition or coating into its plurality of micropores, wherein the microporous size is preferably about 100 microns or less.

In another preferred embodiment, the intraluminal medical device of the present invention further comprises RF current generating means for generating RF current, wherein the RF current generating means is connected to the intraluminal medical device and is adapted for delivering RF current to the intraluminal medical device. The intraluminal medical device may further comprise temperature-sensing means positioned at close proximity of the exterior surface of the intraluminal medical device for measuring tissue temperature, wherein said temperature-sensing means comprises a thermocouple or a thermister-measuring probe. The intraluminal medical device may still further comprise temperature control means for receiving temperature readings, wherein the temperature readings sensed from the temperature sensing means is relayed to the temperature control means and is adapted to effect the RF current delivery to the intraluminal medical device. The RF current is preferred within the range of 50 to 2,000 kHz.

Briefly, heat is generated by supplying a RF energy source to the surface fluorinated intraluminal medical stent, which is comprised of one electrode means in contact with the body tissues. The "electrode means" in this invention is defined to comprise an implantable stent, grafted stent, or a temporary stent capable of contacting the underlying tissue in an appropriate tissue site when the stent is deployed. The RF energy can be applied to the electrode means and consequently to the tissues. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. The generator should be grounded to avoid electrical interference. Heat is controlled by the power of the RF energy delivered, the delivery mode, and by the delivery duration. The standard RF energy generator means and its applications through electrode means, to a patient are well known for those who are skilled in the art.

A method for treating an intraluminal tissue of a patient comprises the steps of positioning an intraluminal medical device at an appropriate intraluminal tissue site, wherein the intraluminal medical device comprises an elongate radially expandable tubular stent or grafted stent having an interior luminal surface and an opposite exterior surface extending along a longitudinal stent axis, and wherein the exterior surface, the interior surface, and/or the entire surface of the expandable tubular stent has fluorine-containing coating. The method further comprises deploying the radially expandable tubular stent. In an alternate embodiment, the method comprises collapsing the radially expandable tubular stent and retracting the collapsed stent from a body of a patient.

The method for treating an intraluminal tissue of a patient further comprises applying RF current to the intraluminal medical device to effect treatment of the intraluminal tissue, wherein the intraluminal medical device further comprises RF current generating means for generating RF current, wherein the RF current generating means is connected to the intraluminal medical device and is adapted for delivering RF current to the intraluminal medical device. Alternately, the method further comprises measuring tissue temperature, wherein the intraluminal medical device further comprises temperature sensing means positioned at close proximity of the exterior surface of the intraluminal medical device, and wherein said temperature sensing means comprises a thermocouple or a thermister measuring probe. The method still further comprises relaying measured temperature from the temperature sensing means to a temperature control means, wherein the temperature sensed is adapted to effect the RF current delivery to the intraluminal medical device.

The method and intraluminal medical device of the present invention has several significant advantages over other known systems to treat the intraluminal tissues. In particular, the intraluminal medical device comprising the surface fluorinated stent and/or the RF energy therapy means results in a more efficient therapeutic effect having substantial reduction in re-stenosis.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of a fluorinated stent and methods thereof.

Figure 1:
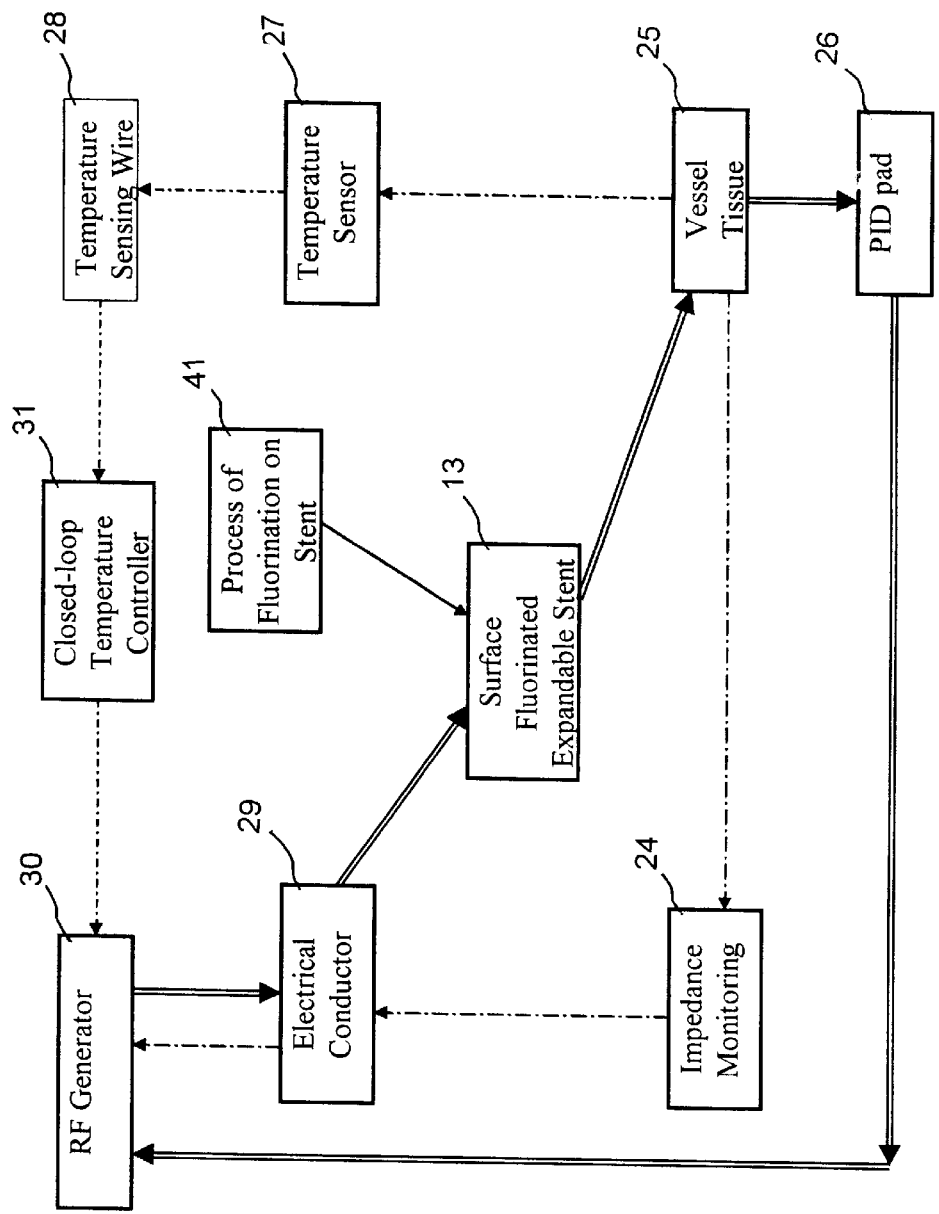
FIG. 1 is a schematic diagram of a RF treatment method in relation to an intraluminal tissue through an intraluminal medical device having a surface fluorinated stent.

FIG. 1 shows a schematic diagram of a RF treatment method in relation to an intraluminal tissue through an intraluminal medical device comprising an elongate radially expandable tubular stent having an interior luminal surface and an opposite exterior surface extending along a longitudinal stent axis, wherein the exterior surface, the interior surface and/or the entire surface of the expandable tubular stent has fluorine-containing coating. A RF generator 30 is connected to a surface fluorinated expandable stent 13 through an electrical conductor 29. In one embodiment, the stent 13 is to contact the underlying tissue 25 at a stent deployed state. A DIP (dispersive indifferent pad) type pad 26, that contacts a patient, is connected to the Indifferent Electrode Connector on the RF generator 30. Therefore, the RF energy delivery becomes effective when a close circuit from a RF generator 30 through a stent, a patient and returning to the RF generator is formed. Impedance 24 measured from the tissue contact is to ensure good tissue contact for ablation through the stent 13, otherwise the RF power is cutoff when the impedance is unreasonably beyond the acceptance value. A temperature sensor 27 may also used to measure the tissue temperature and is relayed through a temperature sensing wire 28 and a closed-loop temperature controller 31 for controlling the ablative energy delivered. Heat is controlled by the power of the RF energy delivered and by the delivery duration.

Figure 2:
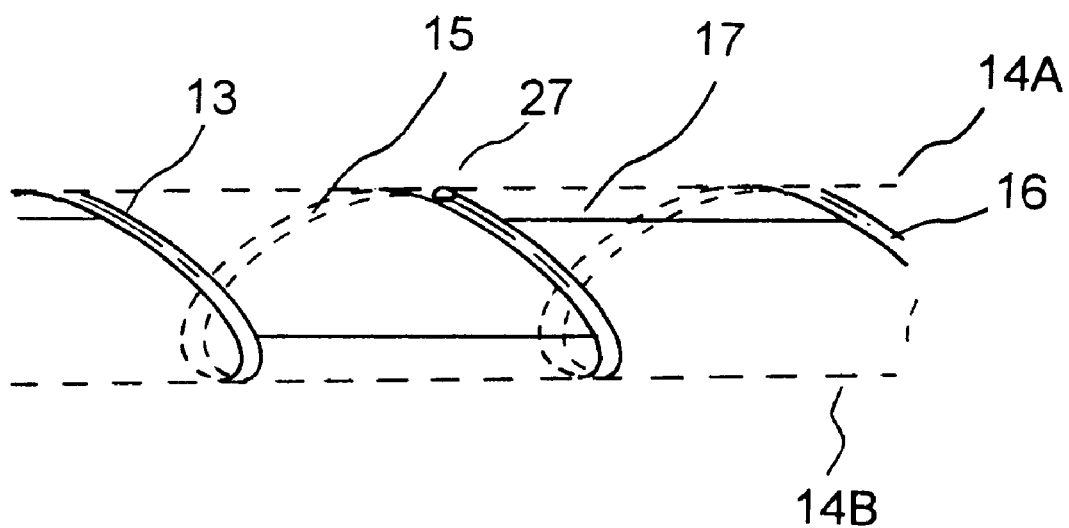
FIG. 2 is an overall view of a preferred elongate radially expandable tubular stent having a fluorinated stent surface at a non-deployed state, constructed in accordance to the principles of the present invention.

FIG. 2 shows an overall view of a preferred elongate radially expandable tubular stent 13 having a fluorinated stent surface at a non-deployed state, constructed in accordance to the principles of the present invention. As shown in FIG. 2, the stent 13 has its radially outer boundaries 14A, 14B at a non-deployed state. The interior luminal surface 15, the exterior surface 16, or an entire surface of the stent 13 may be fluorinated or comprise fluorine-containing compounds. The interior luminal surface 15 is to contact a body fluid, such as blood in a vascular stenting procedure, while the exterior surface 16 is to contact tissue when the stent 13 is deployed to support and enlarge the biological vessel or duct.

In an alternate embodiment, an optional reinforcing wire 17 that connects two or more of the adjacent members or loops of the stent structure 13 is used to lock-in and/or maintain the stent at its expanded state when a stent is deployed. This reinforcing wire 17 may be made of a Nitinol or other high strength material. A Nitinol device is well known to have a preshape and a transition temperature for said Nitinol device to reverse to its preshape. One method for treating an intraluminal tissue of a patient using a surface fluorinated stent 13 of the present invention comprises collapsing the radially expandable tubular stent and retracting the collapsed stent from a body of a patient. Said operation for collapsing a radially expandable tubular stent may be accomplished by elevating the temperature for the reinforcing wire 17 to beyond its transition temperature so that the reinforcing wire 17 is reversed to its straightened state or other appropriate state to cause the stent 13 to collapse for removing said stent from the body of a patient.

Figure 3:
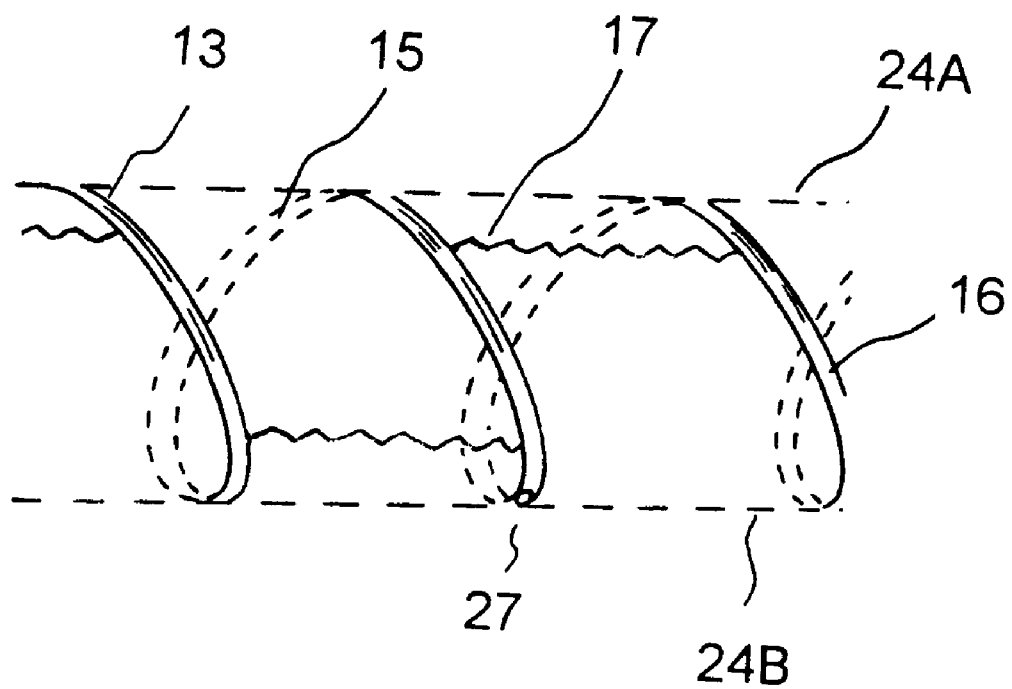
FIG. 3 is an overall view of a preferred elongate radially expandable tubular stent having a fluorinated stent surface at a deployed state, constructed in accordance to the principles of the present invention.

FIG. 3 shows an overall view of a preferred elongate radially expandable tubular stent 13 having a fluorinated stent surface at a deployed state, constructed in accordance to the principles of the present invention. As shown in FIG. 3, the stent 13 has its radially outer boundaries 24A, 24B at a deployed state. The interior luminal surface 15, the exterior surface 16, or an entire surface of the stent 13 may be fluorinated or may comprise fluorine-containing compounds. The interior luminal surface 15 is to contact a body fluid, such as blood in a vascular stenting procedure, while the exterior surface 16 is to contact tissue when the stent 13 is deployed to support and enlarge the biological vessel. The reinforcing wire 17 may be used to maintain the expanded stent at its expanded state as a permanent stent or as a temporary stent. In the case of the surface fluorinated stent 13 functioning as a temporary stent, the reinforcing wire 17 may have the capability to cause collapsing of the expanded stent. In either case, the stent may function as "electrode means" for RF energy delivery to the underlying tissue 25.

The deployment of a stent can be accomplished by a balloon on a delivery catheter or by self-expanding after a pre-stressed stent is released from a delivery catheter. A delivery catheter for stent deployment and mechanisms of stent deployment are well known to one who is skilled in the art. The expandable stent 13 may be a self-expandable stent, a balloon-expandable stent or an expandable-retractable stent. The expandable stent may be made of a memory coil, mesh material, and the like.

In one embodiment, at least one temperature sensor 27 is disposed at close proximity of the expandable stent 13. Insulated temperature sensor wire means 28 passes from the temperature sensor 27, to an external temperature control mechanism 31 that is connected to a RF generator 30. The RF energy delivery is controlled by using the measured temperature from the at least one temperature sensing means 27, through a closed-loop temperature control mechanism and/or algorithm. When the measured temperature rises to a preset high-limit point, the temperature control mechanism sends out a signal to cut off the RF energy supply. In a similar manner, when the measured temperature drops to a preset low-limit point, the temperature control mechanism sends out a signal to activate the RF energy supply.

Figure 4:
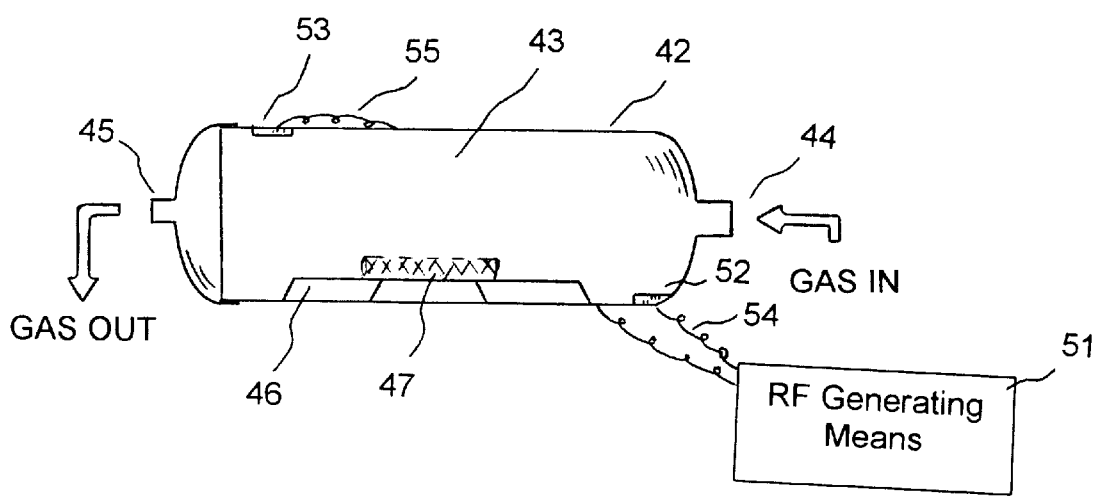
FIG. 4 is a schematic diagram of a preferred fluorination process for making a fluorinated stent via glow discharge method.

The intraluminal medical device comprises the fluorine-containing coating, wherein the coating is selected from a group consisting of glow discharge coating, adhesive coating, impregnating coating, compound coating, dip coating, paste coating, and sintering. FIG. 4 shows a schematic diagram of a preferred fluorination process 41 for making a fluorinated stent via glow discharge method. A fluorination reaction vessel 42 comprises a vacuum chamber 43, a gas inlet port 44, a gas outlet port 45, a supporting stand 46 for the device 47 (e.g. a stent 13) to be fluorinated, and a radiofrequency generating means 51 having a bipolar electrode setup 52, 53 and its associated conducting wires 54, 55 to create a RF field for glow discharging fluorine-containing plasma onto the surface of said device 47. The fluorination process via glow discharge method is well known to one who is skilled in the art. The major parameters for operation include the radiofrequency power level, the fluorine-containing gas used, the concentration of the gas, the degree of vacuum prior to gas introduction, and the configuration of the device to be fluorinated.

A process for making a surface of an intraluminal medical device biocompatible comprises surface treatment means for coating a fluorine-containing material oil surface of the intraluminal medical device to make a surface fluorinated medical device, wherein the intraluminal medical device is an elongate radially expandable tubular stent or grafted stent having an interior luminal surface and an opposite exterior surface extending along a longitudinal stent axis. The surface is selected from a group consisting of an interior luminal surface, an exterior surface or an entire surface of the intraluminal medical device. The surface treatment means for coating a fluorine-containing material on the surface of the intraluminal medical device is selected from a group consisting of glow discharge coating, impregnating coating, compound coating, adhesive coating, dip coating, paste coating, sintering, and the like.

A method for treating an intraluminal tissue of a patient, the method comprises the steps of (a) positioning an intraluminal medical device at an appropriate intraluminal tissue site, the intraluminal medical device comprising an elongate radially expandable tubular stent having an interior luminal surface and an opposite exterior surface extending along a longitudinal stent axis, wherein the exterior surface, the interior luminal surface or an entire surface of the expandable tubular stent has fluorine-containing coating; and (b) deploying the radially expandable tubular stent.

The method for treating an intraluminal tissue of a patient further comprises applying RF current to the intraluminal medical device to effect treatment of the intraluminal tissue, wherein the intraluminal medical device further comprises RF current generating means for generating RF current, wherein the RF current generating means is connected to the intraluminal medical device and is adapted for delivering RF current to the intraluminal medical device. The method further comprises measuring temperature, wherein the intraluminal medical device further comprises temperature sensing means positioned at close proximity of the exterior surface of the intraluminal medical device, and wherein said temperature sensing means comprises a thermocouple or a thermister measuring probe. The method may further comprise relaying measured temperature from the temperature sensing means to a temperature control means, wherein the temperature sensed is adapted to effect the RF current delivery to the intraluminal medical device.

The external RF current generator means has the capability to supply RF current by controlling the time, power, and temperature through an optional separate closed-loop temperature control means. The patient is connected to the RF generator means through a DIP electrode to form a closed-loop RF current system. Therefore, RF energy is applied and delivered to the targeted tissue region, through the expandable stent or metallic member of this invention. The radiofrequency energy current in this invention is preferably within the range of 50 to 2,000 kHz.

In a particular embodiment, the stent for the RF current delivery of this invention consists of conductive metals such as platinum, iridium, gold, silver, stainless steel, Nitinol, or an alloy of these metals. The elongate radially expandable tubular stent in this invention is selected from group consisting of a grafted stent, a coil stent, a mesh stent, a scaffold stent, a sleeve stent, a porous stent, and a permeable stent.

From the foregoing description, it should now be appreciated that a surface fluorinated stent for providing an essentially non-thrombogenic and biocompatible surface has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An intraluminal medical device comprising:
    an elongate radially expandable tubular stent having an interior luminal surface and an opposite exterior surface extending along a longitudinal stent axis;
    the exterior surface of the expandable tubular stent having fluorine-containing coating.

2. The intraluminal medical device of claim 1, wherein the interior luminal surface of the elongate radially expandable tubular stent has fluorine-containing coating.

3. The intraluminal medical device of claim 1, wherein an entire surface of the elongate radially expandable tubular stent has fluorine-containing coating.

4. The intraluminal medical device as in claim 1 further comprising temperature sensing means positioned at close proximity of the exterior surface of the intraluminal medical device for measuring temperature, wherein said temperature sensing means comprises a thermocouple or a thermister measuring probe.

5. The intraluminal medical device as in claim 4 further comprising temperature control means for receiving temperature readings, wherein the temperature readings sensed from the temperature sensing means is relayed to the temperature control means and is adapted to effect the RF current delivery to the intraluminal medical device.

6. The intraluminal medical device as in claim 1, wherein the RF current is within the range of 50 to 2,000 kHz.

7. The intraluminal medical device of claim 1, wherein the fluorine-containing coating is selected from a group consisting of glow discharge coating, adhesive coating, impregnating coating, compound coating, dip coating, paste coating, and sintering.

8. The intraluminal medical device of claim 1, wherein the elongate radially expandable tubular stent is selected from a group consisting of a grafted stent, a coil stent, a mesh stent, a scaffold stent, a sleeve stent, a porous stent, or a permeable stent.

9. A method for treating an intraluminal tissue of a patient, the method comprising the steps of:

(a) positioning an intraluminal medical device at an appropriate intraluminal tissue site, the intraluminal medical device comprising an elongate radially expandable tubular stent having an interior luminal surface and an opposite exterior surface extending along a longitudinal stent axis, wherein the exterior surface of the expandable tubular stent has fluorine-containing coating; and (b) deploying the radially expandable tubular stent.

10. The method for treating an intraluminal tissue of a patient as in claim 9, the intraluminal medical device further comprising an entire surface of the expandable tubular stent having fluorine-containing coating.

11. The method for treating an intraluminal tissue of a patient as in claim 9, the method further comprising measuring temperature, wherein the intraluminal medical device further comprises temperature sensing means positioned at close proximity of the exterior surface of the intraluminal medical device, and wherein said temperature sensing means comprises a thermocouple or a thermister measuring probe.

12. The method for treating an intraluminal tissue of a patient as in claim 11, the method further comprising relaying measured temperature from the temperature sensing means to a temperature control means, wherein the temperature sensed is adapted to effect the RF current delivery to the intraluminal medical device.

13. The method for treating an intraluminal tissue of a patient as in claim 9 further comprising collapsing the radially expandable tubular stent and retracting the collapsed stent from a body of a patient.

14. The method for treating an intraluminal tissue of a patient as in claim 9, wherein the elongate radially expandable tubular stent is selected from group consisting of a grafted stent, a coil stent, a mesh stent, a scaffold stent, a sleeve stent, a porous stent, and a permeable stent.

* * * * *